(12) United States Patent
Lu

(10) Patent No.: US 7,931,617 B2
(45) Date of Patent: *Apr. 26, 2011

(54) SAFETY SYRINGE

(76) Inventor: Feng-Hui Lu, Kaohsiung (TW)

( * ) Notice: Subject to any disclaimer, the term of this patent is extended or adjusted under 35 U.S.C. 154(b) by 1449 days.

This patent is subject to a terminal disclaimer.

(21) Appl. No.: 11/349,189

(22) Filed: Feb. 8, 2006

(65) Prior Publication Data

US 2007/0185447 A1     Aug. 9, 2007

(51) Int. Cl.
*A61M 5/00* (2006.01)

(52) U.S. Cl. .................................................. 604/110

(58) Field of Classification Search .............. 604/110, 604/187, 192, 198; 128/919
See application file for complete search history.

(56) References Cited

U.S. PATENT DOCUMENTS

| 5,049,133 A * | 9/1991 | Villen Pascual ............... 604/110 |
| 7,611,489 B2 * | 11/2009 | Lu .................................. 604/110 |

* cited by examiner

*Primary Examiner* — Theodore J Stigell
(74) *Attorney, Agent, or Firm* — Muncy, Geissler, Olds & Lowe, PLLC

(57) ABSTRACT

A safety syringe includes a barrel, a push rod, a driving module, and a needle mount. The barrel includes a hollow passage and a barrel cover, and the push rod includes a pad disposed around a distal portion and pushed tightly along the hollow passage of the barrel, and the barrel cover includes a plunger, a driving module of a piston pump, and a needle mount having a cut surface at the piston pump, such that the distal portion of the push rod pushes the plunger to move forward, while the cut surface of the distal portion and the cut surface of the needle mount are pressed to separate with each other, and the plunger continues moving forward to offset the air pressure therein, so as to retract the needle mount into a push rod accommodating cavity to accommodate the needle safely after an injection is taken place.

6 Claims, 6 Drawing Sheets

SAFETY SYRINGE

FIELD OF THE INVENTION

The present invention relates to a safety syringe, and more particularly to a syringe that uses a distal portion and a needle mount having a cut surface each and pressing with each other for separations to operate together with a plunger that continues pushing and offsetting the air pressure therein, so as to push a needle mount to retract into a push rod accommodating cavity to achieve a safety accommodating effect.

BACKGROUND OF THE INVENTION

In the present medical technology area, it is common to use a syringe for needle injections, wherein a liquid medicine is contained in a syringe, and a push rod installed in a hollow external rod is used to push the liquid medicine in the syringe to discharge from a distal portion of the syringe, and thus syringes are used extensively in medical area.

At present, there is a common syringe having an external rod, a push rod, and a needle mount. If the syringe is used for a needle injection for medical treatments, the push rod of the syringe can directly drive the liquid medicine contained in the syringe to flow out from the distal portion of the syringe by using a pushing force. However, the use of a prior art syringe still has the following problems to be solved:

1. The prior art syringe is unsafe. If the syringe is used for injecting a liquid medicine into a human body and the syringe does not come with a safety design for containing the needle in an injection process, the needle will be exposed from a needle cap after an injection, and a user may get a needle stick by accident easily which will result in tremendous damages.

2. The effect of using a prior art syringe is poor. Since the syringe has an injection function and the needle of the syringe has a protruding design, therefore it is necessary to cover the needle by a needle cap after an injection has taken place. Medical professionals have to firmly remember and strictly follow the procedure, and thus a needle stick may occur easily and it is difficult to reduce the chance of preventing medical professionals from being infected by a used needle.

SUMMARY OF THE INVENTION

The primary objective of the present invention is to provide a safety syringe using a distal portion of a push rod to push a plunger of a driving module forward while a cut surface of the distal portion and a cut surface of a needle mount press with each other for separation, after an injection is conducted by a medical professional. The plunger keeps on pushing to offset the air pressure therein, so as to drive the needle mount to retract into an accommodating cavity of the push rod, and the needle can be accommodated safely after an injection is taken.

To achieve the foregoing objective, the technical measure taken by the present invention is to provide a safety syringe, comprising a barrel, a push rod, a driving module, and a needle mount. The barrel has a hollow passage and a barrel cover. A pad is disposed around the periphery of the distal portion of the push rod is closely attached to a hollow passage of the barrel for the pushing action, and a driving module is installed in the barrel cover and has a plunger and a piston pump, and the piston pump of the driving module has a needle mount with a cut surface.

By the aforementioned structural design, the safety syringe can achieve the following effects:

1. The safety syringe is safe. The syringe uses the distal portion of the push rod to drive the plunger of the driving module to move forward, while pressing the cut surface of the distal portion and the cut surface of the needle mount with each other for separation, and working together with the plunger that keeps pushing and offsetting the air pressure therein, so as to drive the needle mount to retract into the accommodating cavity of the push rod. As a result, the needle can be accommodated after an injection is taken, and thus the safety syringe can provide a very good safety effect.

2. The safety syringe provides a good injection effect. The barrel cover can cover the barrel, such that the needle retracted into the accommodating cavity of the push rod can be sealed by the cap of the barrel cover to greatly reduce the chance of people from being stuck by a needle during recycling or transporting processes to achieve the safety effect.

DETAILED DESCRIPTION OF THE PREFERRED EMBODIMENTS

Figure 1:
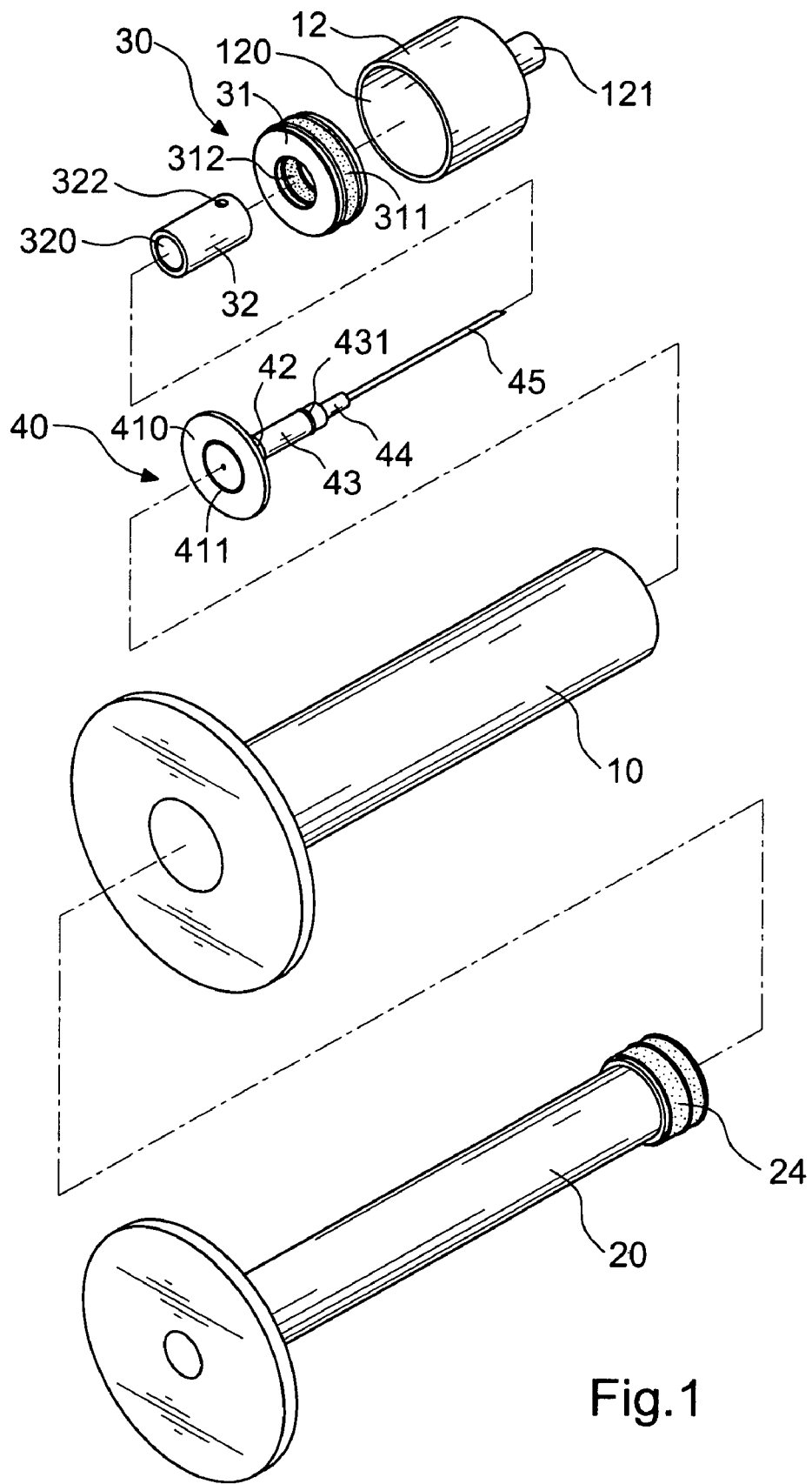
FIG. 1 is an exploded view of a safety syringe of the present invention.
Figure 2:
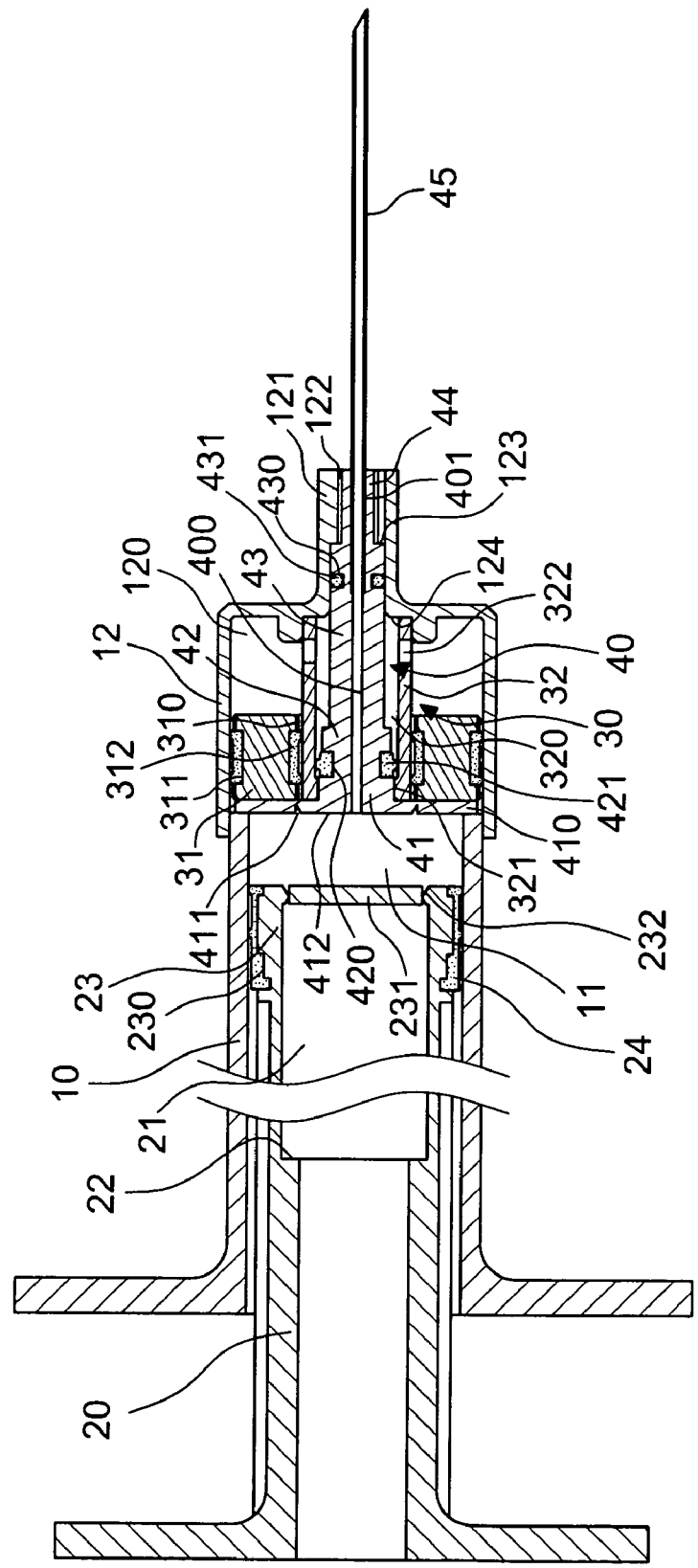
FIG. 2 is a cross-sectional view of a safety syringe of the present invention.

The present invention will now be described in more detail hereinafter with reference to the accompanying drawings as follows:

Referring to FIGS. 1 and 2, a safety syringe of the present invention comprises a barrel 10, a push rod 20, a driving module 30, and a needle mount 40.

The barrel 10 includes a hollow passage 11 therein, and a barrel cover 12 disposed at the distal portion having a protruding end 121 with a chamber 120, and the protruding end 121 includes a perforation 122 therein, and the perforation 122 includes a first pressing surface 123, and an end has a second pressing surface 124 which has a diameter larger than that of the pressing surface 123.

The push rod 20 is disposed and tightly pushed along the hollow passage 11 of the barrel 10 and having an accommodating cavity 21, and the accommodating cavity 21 includes a pressing surface 22, a circular groove 230 disposed around the distal portion 23 and coupled with a pad 24, and a cut surface 231 disposed separately on both distal surfaces of the distal portion 23 and having a concave edge 232.

The driving module 30 is disposed in the barrel cover 12 of the barrel 10 and includes a plunger 31 and a piston pump 32. The plunger 31 has a penetrating hole 310, and the external edge of the plunger 31 and the internal edge of the penetrating hole 310 are connected with the barrel cover 12 and the piston pump 32 respectively by a washer 311, 312. The piston pump 32 is installed in the penetrating hole 310 of the plunger 31 and includes a hollow penetrating hole 320 therein, a flange 321 disposed at an end of the piston pump 32, and a corresponding vent 322 disposed at the periphery of another end of the piston pump 32.

The needle mount 40 is mounted into the piston pump 32 of the driving module 30, and each of a first rod portion 41, a second rod portion 42, a third rod portion 43, and a fourth rod portion 44 has an extended end with different diameters, and each rod portion has a perforation 400 disposed at the middle of the rod and a containing hole 401 disposed at an end for installing a needle 45, wherein the external edge of the first rod portion 41 is engaged with the flange 321 of the piston pump 32, and a seat 410 is extended from the first rod portion 41, and the seat 410 includes a cut surface 412 having a concave edge 411 and disposed at an end for connecting a side of the driving module 30, and the second rod portion 42 includes a circular groove 420 disposed around the periphery of the second rod portion 42 for containing a washer 421 which is propped into the hollow penetrating hole 320 of the piston pump 32, and the third rod portion 43 includes a circular groove 430 disposed around the periphery of the third rod portion 43 for containing a washer 431 which is propped onto the pressing surface 123 at the protruding end 121 of the barrel cover 12, and the fourth rod portion 44 is connected into the perforation 122 at the protruding end 121 of the barrel cover 12.

Figure 3:
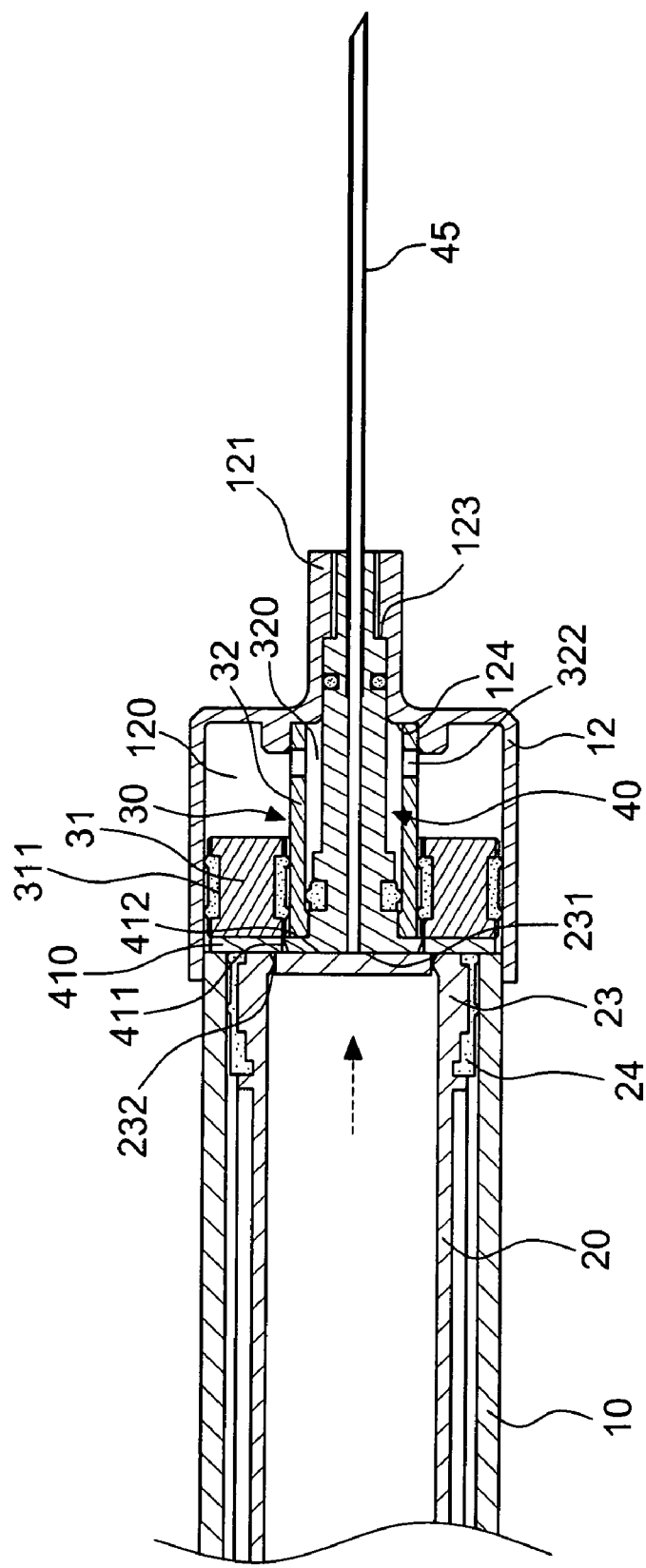
FIG. 3 is a schematic view of pushing a push rod of a safety syringe according to the present invention.
Figure 4:
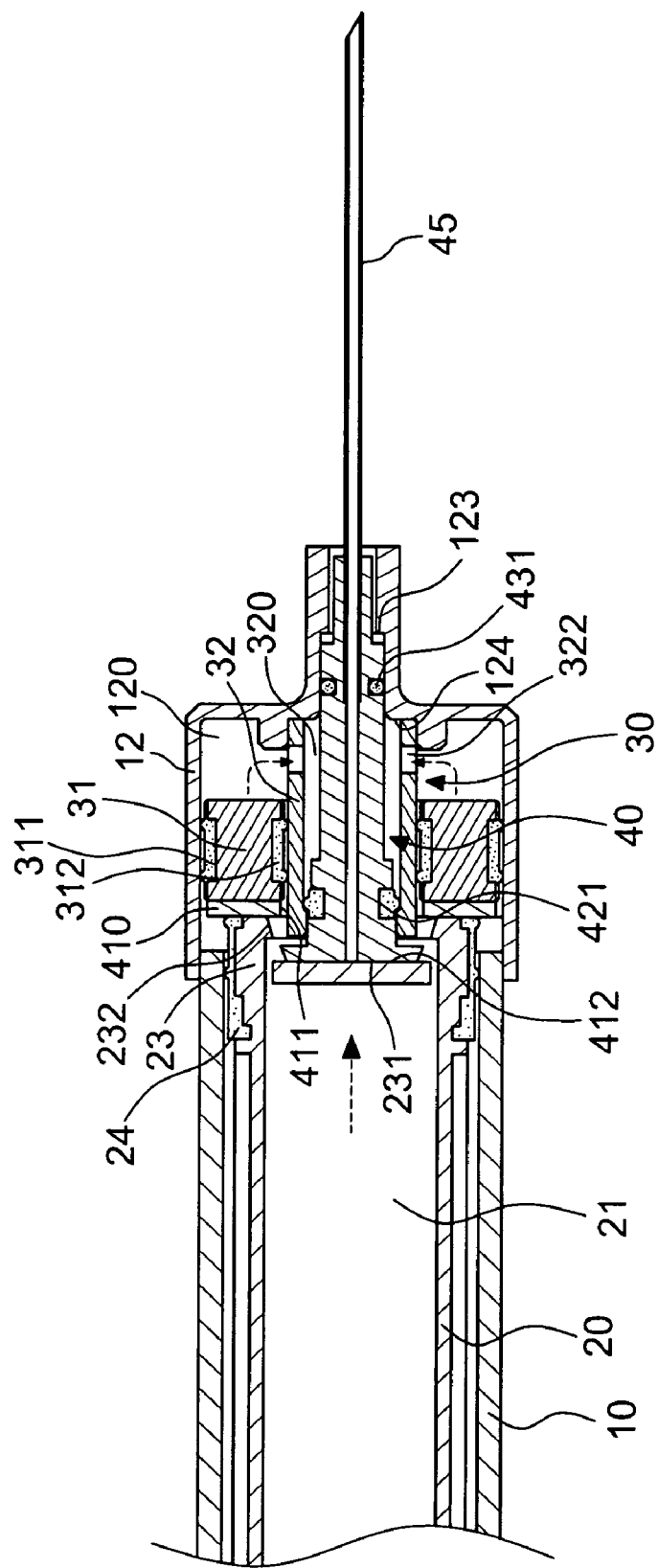
FIG. 4 is another schematic view of pushing a push rod of a safety syringe according to the present invention.
Figure 5:
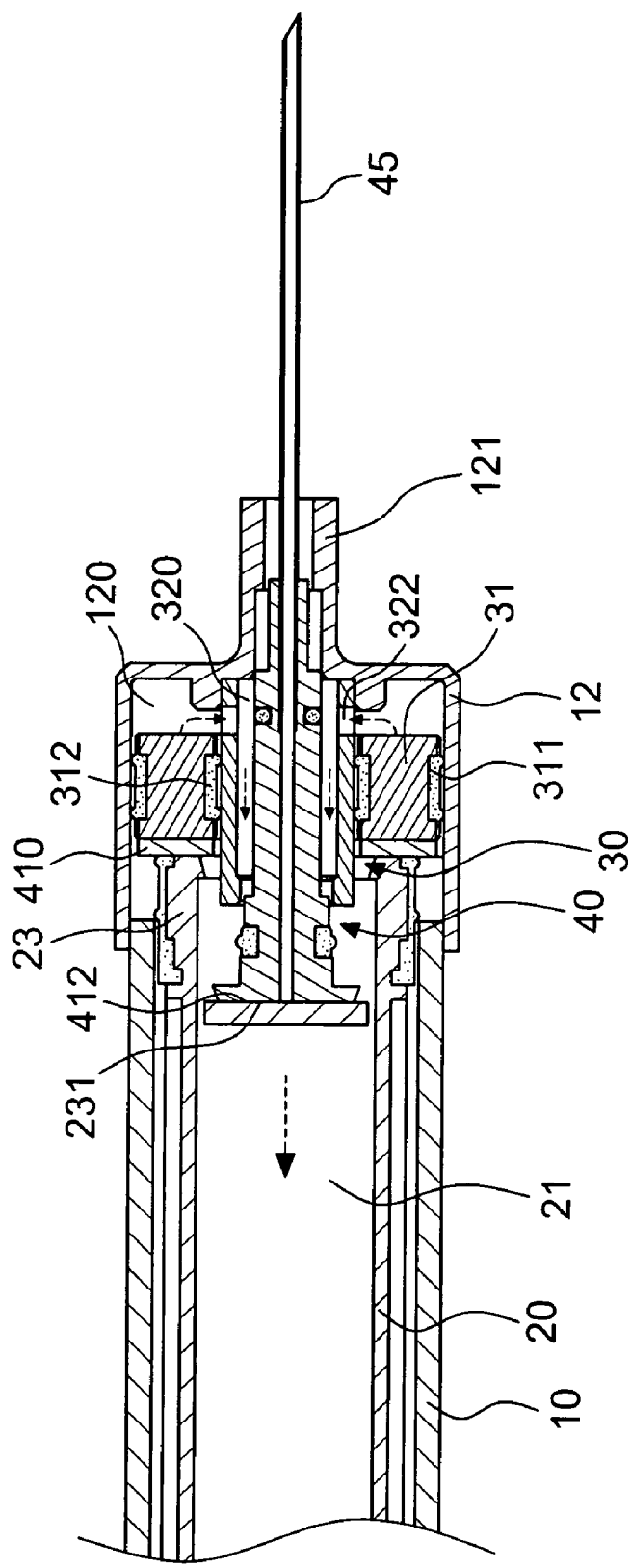
FIG. 5 is a schematic view of accommodating a needle mount of a safety syringe according to the present invention.

Referring to the foregoing figures and FIGS. 3 and 4, if the safety syringe of the invention is used for an injection of a medical treatment purpose, the push rod 20 is pushed from the distal portion 23 of the push rod 20 through an end of the hollow passage 11 of the barrel 10 to another end. If the distal portion 23 of the push rod 20 is in contact with the seat 410 of the needle mount 40 having a driving module 30 at its external edge, such that the distal portion 23 of the push rod 20 props the external edge of the seat 410, the cut surface 231 of the distal portion 23 of the push rod 20 is propped by the third rod portion 43 of the needle mount 40 to press onto the pressing surface 123 of the barrel cover 12 during a push, so that the cut surface 231 of the distal portion 23 of the push rod 20 and the cut surface 412 of the needle mount 40 are separated from the distal portion 23 and the seat 410, due to the disposition of the concave edges 232, 411 and the thickness of the two cut surfaces 231, 412 becomes thinner. Therefore, the two cut surfaces 231, 412 are pressed with each other, and thus the distal portion 23 of the push rod 20 continues moving forward to push the airflow (as indicated by the arrow of FIG. 4) by the plunger 31 of the driving module 30 in the chamber 120 of the barrel cover 12, such that the airflow flows from the corresponding vent 322 at another end of the piston pump 32 into the hollow penetrating hole 320, and the air pressure retracts the needle mount 40 into the accommodating cavity 21 of the push rod 20 (as shown in FIG. 5), and the needle 45 can be accommodated safely after an injection is taken.

Figure 6:
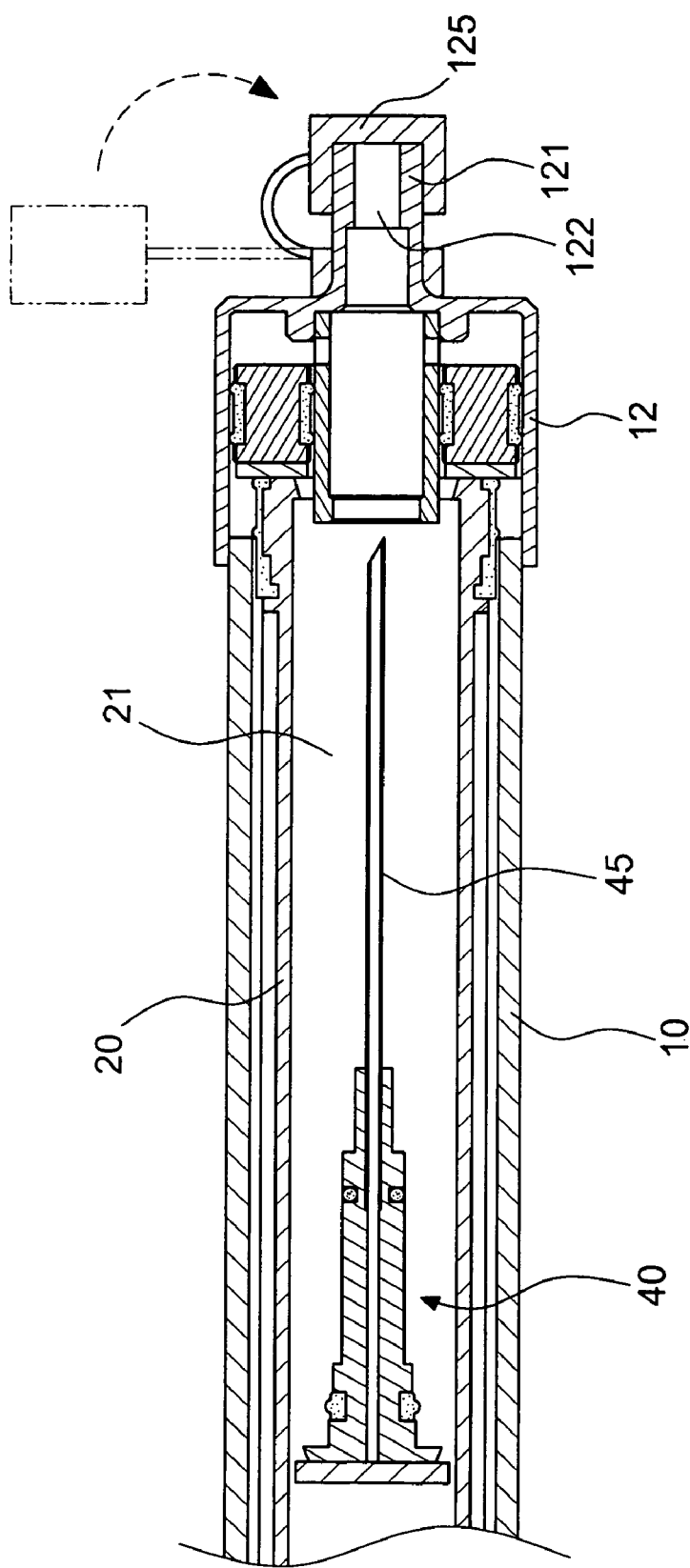
FIG. 6 is a schematic view of adding a cap to a barrel cover of a safety syringe according to the present invention.

Further, the foregoing of the protruding end 121 of the barrel cover 12 could be designed for accommodating the needle 45 into the accommodating cavity 21 of the push rod 20 for preventing a needle stick. Referring to FIG. 6 for a preferred embodiment, the barrel cover 12 includes a cap 125 installable around the periphery of the protruding end 121, such that the cap 125 can be installed onto the protruding end 121 of the barrel cover 12, so as to seal the perforation 122 of the protruding end 121 by using the cap 125 and prevent the protruding end 121 from protruding outward after the needle 45 is accommodated, and thus greatly improving the safety effect and preventing a needle stick during recycling or transportation processes.

From the description above, the safety syringe of the invention can be inserted into a user's body and also can prevent users from being stuck accidentally by the needle 45 of the needle mount 40 to provide a very good safety effect, so that while the distal portion 23 of the push rod 20 is used to push the plunger 31 of the driving module 30 forward after the needle 45 is injected, the cut surface 231 of the distal portion 23 and the cut surface 412 of the needle mount 40 press with each other to separate the distal portion 23 and the seat 410. Further, the plunger 31 continues moving forward to offset the air pressure therein and retract the needle mount 40 into the accommodating cavity 21 of the push rod 20, so as to achieve a better safety effect of accommodating the needle 45.

What is claimed is:

1. A safety syringe, comprising:
   a barrel, having a hollow passage disposed therein, and a barrel cover disposed at a distal portion of said barrel, said barrel cover having a chamber and a protruding end, said protruding end having a first perforation therein;
   a push rod, installed in said hollow passage of said barrel and having an accommodating cavity including a first pressing surface disposed therein, a first circular groove disposed at a periphery of a distal portion of said push rod, and a first cut surface with a first concave edge disposed on a surface of said distal portion of said push rod;
   a driving module, installed in said barrel cover and including a plunger, a piston pump, a first washer and a second washer, said plunger having a penetrating hole, said piston pump having a flange disposed at a first end thereof and a hollow penetrating hole therein, wherein said first washer couples an external edge of said plunger to said barrel cover and said second washer couples an internal edge of said penetrating hole of said plunger to said piston pump;
   a needle mount, installed in said piston pump of said driving module, and having a first rod portion, a second rod portion, a third rod portion, and a fourth rod portion extended from an end of said needle mount, and an external edge of said first rod portion being coupled with said flange of said piston pump, and a periphery of said second rod portion having a second circular groove, such that a third washer is pressed at said hollow penetrating hole of said piston pump, and the periphery of said third rod portion having a third circular groove, such that a fourth washer is pressed onto a second pressing surface of said protruding end of said barrel cover, and said fourth rod portion is disposed in said first perforation of said protruding end of said barrel cover, wherein depression of the push rod causes the push rod to come into contact with the driving module and needle mount such that the first cut surface is separated from the distal portion of the push rod and further depression of the push rod causes air pressure in the chamber to retract the needle mount into the accommodating cavity.

2. The safety syringe of claim 1, wherein said protruding end of said barrel cover includes said first perforation therein, and said first perforation includes said second pressing surface and a third pressing surface thereon.

3. The safety syringe of claim 2, wherein a diameter of said third pressing surface is larger than that of said second pressing surface.

4. The safety syringe of claim 1, wherein said piston pump includes a vent disposed at a second end thereof.

5. The safety syringe of claim 1, wherein said each rod portion of said first rod portion, said second rod portion, said third rod portion, and said fourth rod portion has a second perforation disposed at the middle of the rod portion and a containing hole disposed at an end for installing a needle.

6. The safety syringe of claim 1, wherein said first rod portion includes a seat extended from an end of said first rod portion, and said seat includes a second cut surface with a second concave edge disposed on a lateral side of said seat for connecting a lateral side of said driving module.

* * * * *